United States Patent [19]

Miyazawa et al.

[11] Patent Number: 5,391,494
[45] Date of Patent: Feb. 21, 1995

[54] PROCESS FOR SELECTIVELY PRODUCING OPTICALLY ACTIVE 1-DERIVATIZED-2-DIOL USING LIPASE CES AND TRIGLYCERIDE

[75] Inventors: Kazutoshi Miyazawa; Naoyuki Yoshida, both of Ichihara, Japan

[73] Assignee: Chisso Corporation, Osaka, Japan

[21] Appl. No.: 104,408

[22] Filed: Aug. 10, 1993

Related U.S. Application Data

[60] Continuation of Ser. No. 866,878, Apr. 10, 1992, abandoned, which is a division of Ser. No. 764,072, Sep. 23, 1991, abandoned, which is a continuation of Ser. No. 444,784, Dec. 1, 1989, abandoned.

[30] Foreign Application Priority Data

Dec. 9, 1988 [JP] Japan ................. 63-309832
Apr. 24, 1989 [JP] Japan ................. 1-101689

[51] Int. Cl.6 .................................... C12P 41/00
[52] U.S. Cl. ............................. 435/280; 435/874
[58] Field of Search ......................... 435/280, 874

[56] References Cited

U.S. PATENT DOCUMENTS

| | | | |
|---|---|---|---|
| 4,882,451 | 11/1989 | Yoshida et al. | 556/440 |
| 4,916,074 | 4/1990 | Yoshida et al. | 435/280 |
| 4,996,158 | 2/1991 | Oda et al. | 435/280 |
| 5,256,569 | 10/1993 | Yoshida et al. | 435/280 |

FOREIGN PATENT DOCUMENTS 61-205230 9/1986 Japan .

OTHER PUBLICATIONS

Brown, H. C. et al., J. Org. Chem., 46:3978–88 (1981).
Kirchner, G. et al.; J. Am. Chem. Soc., 107:7072–76 (1985).
Okumura, S., BBA, 575:156–165 (1979).
Hills, M., BBA, 1042:237–240 (1990).
Sonnet, P., JAOCS, 65:900–904 (1988).
Caristen, M., J. Chem. Soc. Chem. Comm., 1988:264–266.
Jones, J., Tetrahedron, 42:3351–3403 (1986).
Hamaguchi, S., Agri. Biol. Chem., 50:375–380 (1986).
Cambou, B., Biotech. Bioeng., XXVI:1449–1454 (1984).
Malanga et al., Synthetic Communications, 12(1), pp. 67–70 (1982).
Mukaiyama et al., Chemistry Letters, 1985, pp. 1359–1362.
Sih et al., Jour. Am. Chem. Soc., vol. 97, No. 4, (1975), pp. 865–874.

*Primary Examiner*—Douglas W. Robinson
*Assistant Examiner*—S. Saucier
*Attorney, Agent, or Firm*—Wenderoth, Lind & Ponack

[57] ABSTRACT

This invention provides optically active compounds which are starting materials of physiologically active substances, functional materials and the like, and the compounds are represented by the general formula (I):

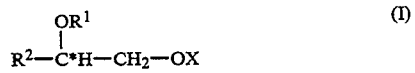

wherein $R^1$ is hydrogen or alkanoyl of 2–20 carbon atoms, $R^2$ is alkyl of 1–40 carbon atoms, alkenyl of 1–40 carbon atoms, or alkynyl of 1–40 carbon atoms in which the alkyl, alkenyl or alkynyl moiety is possible to have phenyl, cyclohexyl, pyridyl, pyrimidyl, pyridadyl, pyrazyl, dioxyl, bicyclooctyl, or a substituent thereof, or halogen, cyanogen, oxygen, nitrogen, silicon or sulfur, and X is a protective group removable by a chemical method of organic synthesis and C* is an asymmetric carbon.

2 Claims, No Drawings

PROCESS FOR SELECTIVELY PRODUCING OPTICALLY ACTIVE 1-DERIVATIZED-2-DIOL USING LIPASE CES AND TRIGLYCERIDE

This application is a continuation of now abandoned application Ser. No. 07/866,878, filed Apr. 10, 1992, which application is a division of now abandoned application Ser. No. 07/764,072, filed Sep. 23, 1991, which application is, in turn, a continuation of now abandoned application Ser. No. 444,784, filed Dec. 1, 1989.

BACKGROUND OF THE INVENTION

The present invention relates to optically active compounds which are starting materials of physiologically active substances, functional materials and the like, and to a process of producing the optically active compounds.

Optically active compounds and their esters are useful compounds as starting materials for physiologically active substances such as pharmaceuticals and agricultural chemicals, functional materials and the like, and as their intermediates. However, the compounds have optical isomers, and in many cases they do not sufficiently exhibit their useful characteristics unless the R- or S-compound is predominant.

For the above reasons, and in order to obtain an optically active substance, it is necessary to optically resolve a racemate (itself typically obtained by a synthetic chemical technique), to conduct an asymmetric synthesis, or to convert from an optically active starting material by a stereochemical synthetic method. In many cases, the process is troublesome and disadvantageous industrially.

Accordingly, it is desired to develop a technique for obtaining optically active compounds by an industrially advantageous method.

SUMMARY OF THE INVENTION

The inventors of the present invention carried out research for obtaining a process for producing optically active compounds by an advantageous industrial method. They found a process for producing an optically active alcohol and an ester, in which the alcohol and the ester are efficiently obtained by using an enzyme.

Namely, the present invention provides a compound represented by the general formula (I):

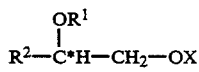
(I)

wherein $R^1$ is hydrogen or alkanoyl of 2–20 carbon atoms, $R^2$ is alkyl of 1–40 carbon atoms, alkenyl of up to 40 carbon atoms, or alkynyl of up to 40 carbon atoms in which the alkyl, alkenyl or alkynyl moiety may have phenyl, cyclohexyl, pyridyl, pyrimidyl, pyridadyl, pyrazyl, dioxyl, bicyclooctyl, or a substituent thereof, or halogen, cyanogen, oxygen, nitrogen, silicon or sulfur, and X is a protective group removable by a chemical method of organic synthesis and C* is an asymmetric carbon.

Further, the present invention provides a process for producing an optically active compound which comprises reacting under substantially anhydrous conditions and in the presence of a hydrolase an ester and a compound represented by the general formula (II):

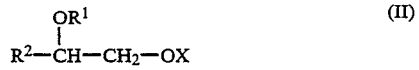

wherein $R^1$, $R^2$ and X have the same meaning as described above, to effect a transesterification reaction, and resolving to an optically active alcohol which has either the R- or S-configuration and the corresponding ester of the S- or R-alcohol.

According to the method of the present invention, the reaction is conducted under substantially anhydrous conditions. This method does not require the use of a small amount of water or a lower alcohol instead of the water, and a side reaction does not occur such as hydrolysis of obtained esters and esters of starting compounds and formation of undesirable esters, so that the enzyme is easily separated after the reaction and reused. Furthermore, since the reaction is conducted under substantially anhydrous conditions, the method can be kept free from contaminant of microorganisms. Accordingly, there is no necessity for preparing special equipment, antiseptics, sterilization treatment, etc. It is possible to conduct the reaction in an open system. Further, the reaction may be conducted in the same or higher substrate concentration in comparison with common organic synthetic reactions.

DETAILED DESCRIPTION OF THE INVENTION

The following description illustrates this invention more specifically.

In the present invention, the (R,S)-compounds of the raw materials can be prepared, for example, by the following process.

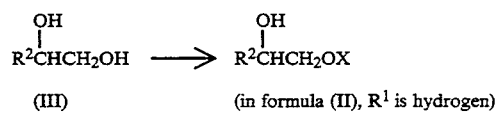

Namely, the (R,S)-compounds can be obtained by introducing a protective group to a commercially available diol compound represented by formula (III).

On the other hand, after a protective group is introduced in an available compound represented by formula (IV), the carbonyl group of the compound is reduced by a reducing agent and the (R,S)-compound (II) can be obtained as shown in the following process.

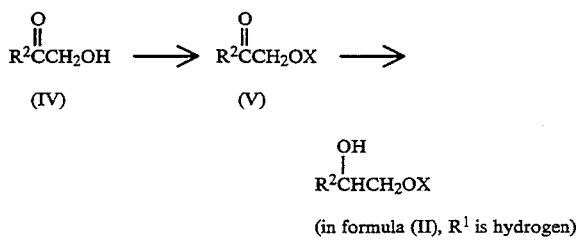

Further, the (R,S)-compounds can be obtained by the following ring opening process of epoxy compounds (VI) which are industrially and inexpensively prepared.

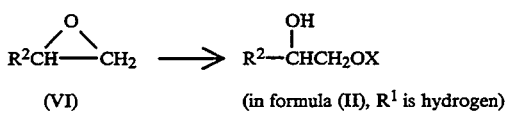

(VI)　　　　　　　(in formula (II), R¹ is hydrogen)

The (R,S)-compounds can be produced by various processes in which common chemical methods of organic synthesis are used.

It is also sufficient to use esters, preferably triglycerides and fatty acid vinyl esters, which are commercially available without any difficulty. As these esters, methyl propionate, ethyl butyrate, ethyl stearate, trichloroethyl laurate, butyl laurate, ethylene glycol diacetate, etc., can be used. Especially, triglycerides and vinylesters are preferable. Triacetin, tripropionin, tributyrin, tricaproin, tristearin, trilaurin, trimyristin, triolein, vinyl acetate, vinyl caproate, vinyl laurate, etc., can be exemplified as such triglycerides and fatty acid vinyl esters.

The hydrolase which is used in this invention has the ability to catalyse a transesterification reaction preferentially between the R- or S-alcohol and the ester when the enzyme is used with the (R,S)-compound, and the enzyme can be used regardless its class. For example a lipase, lipoprotein lipase, esterase, etc. are preferable. The following table shows commercially available enzymes that can be used in the present reaction.

TABLE

| Trade name | Origin | Seller or Maker |
| --- | --- | --- |
| Lipase AP | *Aspergillus niger* | Amano Pharmaceutical Co., Ltd |
| Lipase M | *Mucor javanicus* | Amano Pharmaceutical Co., Ltd |
| Lipase P | *Pseudomonas fluorescens* | Amano Pharmaceutical Co., Ltd |
| Lipase CES | Pseudomonas sp. | Amano Pharmaceutical Co., Ltd |
| Lipase CE | *Humicola lanuginosa* | Amano Pharmaceutical Co., Ltd |
| Lipase F-AP | *Rhizopus javanicus* | Amano Pharmaceutical Co., Ltd |
| Lipase II | *Porcine pancreas* | Sigma Chemical Co., Ltd |
| Lipase VIII | *Geotrichum candidum* | Sigma Chemical Co., Ltd |
| Lipase X | *Rhizopus delamar* | Sigma Chemical Co., Ltd |
| Lipase | *Chromobacterium viscosum* | Toyo Jozo Co., Ltd |
| Palatase A | *Aspergillus niger* | Novo Industi A/S |
| Lipase | *Rhizopus niveus* | Nagase Biochemicals, Co. Ltd |

In addition to these enzymes, microorganisms which produce the enzymes having the above ability can be used regardless of their species and genus. As such microorganisms, the genera Arthrobacter, Acromobacter, Alcaligenes, Aspercillus, Chromobacterium, Candida, Mucor, Pseudomonas, Rhizopus, etc., can be exemplified. The enzymes produced from these microorganisms can be also used.

In the following, the process for producing the optically compounds is described in more detail. In the practice of the invention, the reaction is typically conducted by mixing an (R,S)-compound with an ester, preferably a triglyceride or a fatty acid vinyl ester and efficiently contacting the mixture with an enzyme. The (R,S)-compound and the ester such as the triglyceride or the fatty acid vinyl ester can be used without any particular treatments. When the alcohol is slightly soluble in the ester, an organic solvent such as, for example heptane or toluene can be added. The reaction temperature is suitably 0° to 100° C. and especially preferably 30° to 45° C. The reaction time is broadly 5 to 2000 hours. The reaction time can be shortened by changing the reaction temperature, the kind of the enzyme and the substrate concentration.

The (R,S)-alcohol which is a substrate and the ester are mixed in the ratio 1:0.5 to 1:2 by mole, and preferably 1:1.1 to 1:2 by mole.

After the transesterification reaction, the enzyme can be removed by conventional filter operation and used again, as it is. The filtrate can be separated into an optically active alcohol and an ester which is an antipode of the alcohol, respectively, for instance by distillation or column chromatography. The obtained ester is hydrolyzed in an alkali or acid solution to derive the optically active alcohol which is an antipode of the alcohol.

By the above described process, the optically active R- and S-alcohol can be obtained.

Since the compounds of the present invention represented by formula (I) are diol compounds in which one of hydroxide groups is protected or compounds in which two hydroxide groups are protected by different substituent groups, the compounds can be converted to various types of compounds.

As an example, the compound represented by the general formula (I) wherein R¹ is hydrogen, R² is ethyl and x is

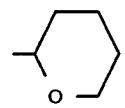

(the same compound as in Example 1) can be easily converted to optically active 3-hydroxypentanoic acid or optically active 2-methyl-3-hydroxypentanoic acid. The obtained compounds are useful as starting materials of serricornin or anhydrous serricornin which is pheromone of *Lasioderma serricorne* (R. W. Hoffmann et al., Tetrahedron Lett., 23, 3479 (1982)).

Moreover, as an example, the compound of the general formula (I) wherein R¹ is hydrogen and R² is n-pentyl can be easily converted to 1-iodo-2-heptanol which is useful for starting materials of prostaglandin (E. J., Corey et al., J. Am. Chem. Soc., 93, 1491 (1971)).

Since the compounds of the general formula (I) can be changed to diol compounds or epoxy compounds, these compounds are useful for starting materials of various compounds.

As an example, optically active epoxy compounds as shown in the following process are useful for starting materials of ferroelectric liquid clystal compounds which are recently noted (Nohira, Kumano, Ishizuka and Miura, 14th Forum of Liquid Crystals, 1B113 (1988)).

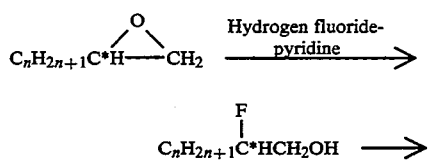

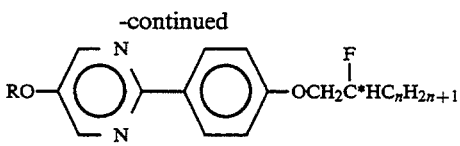

Furthermore, the merits of the production process of the present invention are as follows.

(1) Unnecessary hydrolysis of esters scarcely occurs because the transesterification reaction is substantially conducted under the conditions of no water.

(2) The enzyme can be easily recovered and re-used.

(3) No special equipment and materials are used because the reaction can be performed under the conditions of relatively low temperatures and an open system.

(4) Optically active substances having high purity are obtained by a one-step reaction.

(5) In spite of the biochemical reaction, the substrate concentration can be increased and big reaction vessels are unnecessary, because a buffer solution and the like are not required in the reaction.

DESCRIPTION OF PREFERRED EMBODIMENTS

The following examples illustrate this invention more specifically.

EXAMPLE 1

The preparation of optically active 1-tetrahydropyranyloxy-2-butanol (in formula (I), $R^1$ is hydrogen, $R^2$ is ethyl and X is

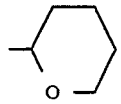

The first step: The preparation of (R,S)-1-tetrahydropyranyloxy-2-butanone

A mixture of 1.00 g of 1-hydroxy-2-butanone, 143 g of 2,3-dihydropyran and 200 ml of dichloromethane was cooled to 0° C. and 4.8 g of pyridine p-toluenesulfonate in 75 ml of dichloromethane was added dropwise to the mixture. The mixture was stirred for four hours in an ice bath and then for one hour at room temperature and left overnight. The obtained solution was cooled in an ice bath. To the solution 3 g of sodium bicarbonate was added. After stirring for one hour, dichloromethane was removed from the solution under reduced pressure. 200 ml of n-heptane was added and the obtained product was purified with a chromatograph over silica gel. After removing the solvent, 174 g of (R,S)-1-tetrahydropyranyloxy-2-butanone was obtained by reduced distillation. b.p. 82° C. (4.5 torr).

The second step: The preparation of (R,S)-1-tetrahydropyranyloxy-2-butanol

A mixture of 38 g of LiAlH$_4$ and one liter of tetrahydrofuran was cooled to 0° C. and 173 g of (R,S)-1-tetrahydropyranyloxy-2-butanone in 450 ml of tetrahydrofuran was added dropwise to the mixture and stirred at room temperature for three hours.

To the reaction product cooled in an ice bath, 300 ml of ethyl acetate, 300 ml of water and 300 ml of aqueous solution of 2N sodium hydroxide were added. After solids were removed by filtration from the reaction system, tetrahydrofuran was removed under reduced pressure from the filtrate. The obtained product was purified with a chromatograph over silica gel. After removing the solvent, 64 g of (R,S)-1-tetrahydropyranyloxy-2-butanol was obtained by reduced distillation.

The third step: The optical resolution of (R,S)-1-tetrahydropyranyloxy-2-butanol A mixture of 10 g of enzyme lipase "Amano" CES (produced by Amano Pharmaceutical Co., Ltd), 60 g of (R,S)-1-tetrahydropyranyloxy-2-butanol and 117 g of tributyrin was reacted with stirring at 38° C. for ten days. After the reaction was stopped, the enzyme was removed by filtration, and the enzyme on the filter paper was washed by using n-heptane. n-Heptane was distilled away from the filtrate, the residue was purified with a chromatograph over silical gel, and 22.5 g of optically active 1-tetrahydropyranyloxy-2-butanol and 20.8 g of 1-tetrahydropyranyloxy-2-butyryloxybutane were obtained.

The obtained compounds were determined by structure analysis of a NMR chart.

EXAMPLE 2

The determination of the optical purity of optically active 1-tetrahydropyranyloxy-2-butanol The first step: The preparation of optically active 1,2-butanediol A mixture of 4.3 g of optically active 1-tetrahydropyranyloxy-2-butanol which was obtained in the third step of Example 1, 0.6 g of pyridine p-toluenesulfonate and 20 ml of ethanol was reacted with stirring for three hours at 60° C.

After ethanol was distilled away from the reacted product under reduced pressure, 0.48 g of optically active 1,2-butanediol was obtained by reduced distillation. b.p. 78° C. (10 torr).

The second step: The preparation of optically active 1,2-butanediol diacetate

To the mixture of 0.48 g of optically active 1,2-butanediol, 5 ml of toluene and 2.5 ml of pyridine, 1.7 g of acetyl chloride was added dropwise in an ice bath and stirred for two hours. 10 ml of water and 10 ml of toluene were added to the reaction mixture and stirred. The obtained solution was washed with 2N sodium hydroxide and then with water. The toluene solution was dried over anhydrous magnesium sulfate. Toluene was distilled away from the solution under reduced pressure, the residue was purified with a chromatograph over silica gel, and 1,2-butanediol diacetate was obtained. The obtained compound had a gas chromatographic purity of 98.9%. It showed a specific rotation of $[\alpha]_D^{28} = -12.2°$ C. (c=1.08, CHCl$_3$). The optical purity of the compound was determined by using a column of optical resolution (Trade name: Chiral Cel OB, produced by Daicel Chemical Industries, Ltd., in Japan). From the peak area of the product, the optical purity was 85% ee.

EXAMPLE 3

The determination of the optical purity of optically active 1-tetrahydropyranyloxy-2-butyryloxybutane The first step: The preparation of optically active 2-butyryloxy-1-butanol A mixture of 9.5 g of optically active 1-tetrahydropyranyloxy-2-butyryloxybutane which was obtained in the third step of Example 1, 1.5 g of pyridine p-toluenesulfonate and 50 ml of ethanol was reacted with stirring for three hours at 60° C. After ethanol was distilled away under reduced pressure, 5.0 g of optically active 2-butyryloxy-1-butanol was obtained by reduced distillation. b.p. 90° C. (4 torr). The second step: The preparation of optically active 1,2-butanediol A mixture of 5.0 g of LiAlH₄ and 30 ml of tetrahydrofuran was cooled to 0° C. 5.0 g of optically active 2-butyryloxy-1-butanol in 15 ml of tetrahydrofuran was added dropwise to the mixture and stirred at room temperature for three hours. To the reaction mixture cooled in an ice bath, 10 ml of ethyl acetate, 10 ml of water and 10 ml of aqueous solution of 2N sodium hydroxide were added. After solids were removed by filtration from the reaction system, tetrahydrofuran was removed under reduced pressure from the filtrate, and 3.4 g of optically active 1,2-butanediol was obtained. The third step: The preparation of optically active 1,2-butanediol diacetate To a mixture of 0.34 g of optically active 1,2-butanediol, 5 ml of toluene and 2.5 ml of pyridine, 1.2 g of acetyl chloride was added dropwise in an ice bath and stirred for two hours. 10 ml of water and 10 ml of toluene were added to the reaction mixture and stirred. The obtained solution was washed with 2N sodium hydroxide and then with water. The toluene solution dried over anhydrous magnesium sulfate. Toluene was distilled away from the solution under reduced pressure, the residue was purified with a chromatograph over silica gel, and 1,2-butanediol diacetate was obtained. The obtained compound had a gas chromatographic purity of 95.0%. It showed a specific rotation of $[\alpha]_D^{30}+14.8(c=1.12, CHCl_3)$.

The optical purity of the compound was determined by using a column of optical resolution (Trade name: Chiral Cel OB, produced by Daicel Chemical Industries, Ltd., in Japan). The antipode of the product was absent and the optical purity was 100% ee.

EXAMPLE 4

The preparation of optically active 1-tetrahydropyranyloxy-2-butanol (in formula (I), R¹ is hydrogen, R² is ethyl and X is

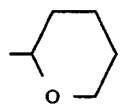

The first step: The optical resolution of (R,S)-1-tetrahydropyranyloxy-2-butanol A mixture of 23 g of enzyme lipase "Amano" CES (produced by Amano Pharmaceutical Co., Ltd), 40 g of (R,S)-1-tetrahydropyranyloxy-2-butanol and 16.5 g of vinyl caproate was reacted with stirring at 38° C. for eight hours. After the reaction was stopped, the enzyme was removed by filtration, and the enzyme on the filter paper was washed by using n-heptane. n-Heptane was distilled away from the filtrate, the residue was purified with a chromatograph over silical gel, and 21.5 g of optically active 1-tetrahydropyranyloxy-2-butanol and 23 g of 1-tetrahydropyranyloxy-2-caproyloxybutane were obtained.

The optical purity of the obtained compounds which was determined by using the same method as in Examples 2 and 3 was 67.6% ee and 100% ee, respectively.

We claim:

1. A process for producing an optically active compound which comprises reacting under substantially anhydrous conditions and in the presence of Lipase CES to catalyze the reaction, a triglyceride and a compound represented by the formula (II):

wherein R² is alkyl of 2–5 carbon atoms, and X is tetrahydropyranyl, to effect a transesterification reaction, and resolving to an optically active alcohol which has either the R- or S-configuration and the corresponding ester of the S- or R-alcohol represented by the formula (I):

wherein R¹ is alkanoyl of 2–20 carbon atoms, R² is alkyl of 2–5 carbon atoms, and X is tetrahydropyranyl, and recovering the optically active alcohol and the corresponding ester.

2. A process as claimed in claim 1, wherein R² is ethyl.

* * * * *